(12) United States Patent
Barco

(10) Patent No.: US 8,680,326 B2
(45) Date of Patent: Mar. 25, 2014

(54) PHARMACEUTICAL COMPOSITIONS AND THERAPEUTIC APPLICATIONS OF A HYDROCORTISONE DERIVATIVE DESIGNATED AS DEINA

(76) Inventor: Giovanni Barco, Pisa (IT)

(*) Notice: Subject to any disclaimer, the term of this patent is extended or adjusted under 35 U.S.C. 154(b) by 0 days.

(21) Appl. No.: 13/511,968

(22) PCT Filed: Nov. 26, 2010

(86) PCT No.: PCT/IB2010/055455
§ 371 (c)(1),
(2), (4) Date: May 24, 2012

(87) PCT Pub. No.: WO2011/064753
PCT Pub. Date: Jun. 3, 2011

(65) Prior Publication Data
US 2012/0283327 A1  Nov. 8, 2012

(30) Foreign Application Priority Data
Nov. 27, 2009 (IT) .................. PI2009A0151

(51) Int. Cl.
*A01N 37/08* (2006.01)
*A61K 31/19* (2006.01)
*A01N 37/00* (2006.01)
*A01N 45/00* (2006.01)
*A61K 31/56* (2006.01)

(52) U.S. Cl.
USPC ........... 562/499; 514/573; 514/574; 514/169; 514/179

(58) Field of Classification Search
USPC ............................. 514/573, 57, 575, 169, 179
See application file for complete search history.

(56) References Cited

U.S. PATENT DOCUMENTS 2,951,074 A   8/1960   Chemerda et al.

FOREIGN PATENT DOCUMENTS

| EP | 1 619 200 A1 | 1/2006 | |
|---|---|---|---|
| WO | WO 2006/051287 A1 | 5/2006 | |
| WO | WO 2009/044251 A2 | 4/2009 | |
| WO | WO 2009044251 A2 * | 4/2009 | ............. A61K 31/19 |

OTHER PUBLICATIONS

Stedman's Medical Dictionary 26th Edition. pp. 1134-1135. Published 1995.*
Dykes, P.J., et al. British Journal of Dermatology vol. 101 pp. 599-609. Published 1979.*
Budel, V.M., et al. Anticancer Research. vol. 6 pp. 709-712. Published 1986.*
Elewski, B., Clinics in Dermatology vol. 27 pp. S48-S53. Published 2009.*
Gupta, A.K. et al. Expert Opinion Pharmacotherapy. vol. 5 pp. 1755-1765. Published 2004.*
Squier, C.A., et al. Critical Reviews in Oral Biology and Medicine. vol. 2, pp. 13-32. Published 1991.*
Weisberg, L.A., et al. Essentials of Clinical Neurology: Diseases of the Peripheral Nerves and Motor Neurons. pp. 16-1 to 16-16. https://tulane.edu/som/departments/neurology/programs/clerkship/upload/wch16.pdf Published online 2005.*
MacMahon, P.J. et al., Radiology vol. 252 pp. 647-661. Published Sep. 2009.*
Costa, AM et al. "Mechanical Forces Induce Scar Remodeling: Study in Non-Pressure-Treated versus Pressure-Treated Hypertrophic Scars", American Journal of Pathology, vol. 155, No. 5, Nov. 1999, pp. 1671-1679.
French, MM et al. "Expression of the Heparan Sulfate Proteoglycan, Perlecan, during Mouse Embryogenesis and Perlecan Chondrogenic Activity In Vitro", Journal of Cell Biology, vol. 145, No. 5, May 31, 1999, pp. 1103-1115.
Rabinovitch, M. et al. "Cell Shape Changes Induced by Cationic Anesthetics", Journal of Experimental Medicine, vol. 143, 1976, pp. 290-304.
Robinson, M. et al. "In Vivo Induction of Hair Growth by Dermal Cells Isolated from Hair Follicles After Extended Organ Culture", J Invest Dermatol., vol. 117, vol. 3, Sep. 2001, pp. 596-604.
Chun, MR et al. "Differential Effects of High-carbohydrate and High-fat Diet Composition on Muscle Insulin Resistance in Rats", J Korean Med Sci, vol. 25, 2010, pp. 1053-1059.
Kali, R. et al. "Improvement of Natrually Aged Skin With Vitamin A (Retinol)", Arch Dermatol, vol. 143, May 2007, pp. 606-612.
International Search Report for corresponding International Patent Application No. PCT/IB2010/055455 mailed Mar. 28, 2011.

* cited by examiner

*Primary Examiner* — Paul Zarek
*Assistant Examiner* — George W Kosturko
(74) *Attorney, Agent, or Firm* — Merchant & Gould P.C.

(57) ABSTRACT

The hydrocortisone derivative of formula (I), whose IUPAC name is 3-[3,5-Dihydroxy-3-(2-hydroxy-acetyl)-3a,6-dimethyl-7-oxo-dodecahydro-cyclo-penta[alpha]naphthalen-6-yl]-propionic acid, designated as Deina®, is used in the treatment of atrophic tissues, particularly skin, cartilage, connective, and mucosal tissues and scalp skin.

10 Claims, No Drawings

PHARMACEUTICAL COMPOSITIONS AND THERAPEUTIC APPLICATIONS OF A HYDROCORTISONE DERIVATIVE DESIGNATED AS DEINA

This application is a National Stage Application of PCT/IB2010/055455, filed 26 Nov. 2010, which claims benefit of Serial No. PI2009A000151, filed 27 Nov. 2009 in Italy and which applications are incorporated herein by reference. To the extent appropriate, a claim of priority is made to each of the above disclosed applications.

This invention relates to new therapeutic applications of a hydrocortisone derivative, specifically Deina. More particularly the invention relates to the use of this derivative in the regeneration of atrophic tissues. The invention also relates to pharmaceutical compositions comprising Deina as the active ingredient and their therapeutic applications.

The atrophic tissue is particularly a cutaneous tissue, a cutaneous annex, a mucosal tissue or a connective tissue. This invention relates to a composition which is effective in regenerating all atrophic and/or dystrophic and/or inflamed and/or reactively calcified tissues, particularly tissues in which there is a reduction of mass caused by a reduction in the number of cells or their size and/or the loss of local-regional vascularisation and/or local-regional innervation, preferably with an inflammatory component with or without necrosis and with or without reactive calcification.

The composition according to the invention is suitable for preparation in various physical forms and formulations specifically adapted to their intended use, such as cosmetic compositions, cell culture media, pharmaceutical compositions and medical devices for human or veterinary use.

As will be illustrated in detail in the section on examples, the composition according to the invention is effective in the regeneration and eutrophic restoration of atrophic cutaneous tissues, mucosal tissues and connective tissues, both in vitro and in vivo, creating suitable microenvironmental conditions to induce eutrophic tissue regeneration.

STATE OF THE ART

Compositions derived from hydrocortisone have been known for a long time (reference is made for example to U.S. Pat. No. 2,951,074 A and EP 1 619 200 A).

The use of compositions derived from hydrocortisone in the treatment of alopecia is also known (reference is made for example to WO2006051287A1 and WO2009044251 A2).

The use of hydrocortisone derivatives in the treatment of tissue atrophies and their complications is not however known.

The term atrophy includes the lesions which occur when a compressive force applied for a sufficiently long time is greater than the blood pressure in the arteriolar-capillary area, sufficient to cause ischaemia. The atrophy may be physiological or pathological, acute or chronic, with the complications of inflammation and/or reactive calcification, and may occur for various reasons, the main ones being:

reduced use (disuse atrophy) of for example a limb or joint (immobility or cartilaginous lesions),
loss of innervation, as a result of a lesion to a peripheral nerve,
insufficient blood flow (acute or chronic ischaemia),
ageing,
atrophies due to a fall in oestrogen (hormonal malfunctions or menopause) in the field of gynaecology.

At cell level atrophy is characterised by a reduction in the minimum dimensions compatible with the survival of all cell organelles.

This invention relates to therapeutic or cosmetic use of the composition derived from hydrocortisone whose IUPAC name is 3-[3,5-Dihydroxy-3-(2-hydroxy-acetyl)-3a,6-dimethyl-7-oxo-dodecahydro-cyclo-penta[alpha]naphthalen-6-yl]-propionic acid having a molecular weight of 382 Daltons ($C_{20}H_{30}O_7$), designated as Deina®, in the treatment of simple or complicated cutaneous and/or mucosal and/or connective tissue atrophies.

Deina® induces the restoration of a eutrophic condition in cutaneous and/or mucosal and/or connective tissues affected by moderate or severe simple or complicated atrophic conditions giving rise to local-regional tissue regeneration followed by recovery of all harmed tissue-specific functions.

According to this invention this object is achieved through the solution claimed specifically in the following claims. With regard to the invention the claims form an integral part of the technical teaching provided.

SUMMARY OF THE INVENTION

The object of this invention is a new use of the hydrocortisone composition whose IUPAC name is 3-[3,5-Dihydroxy-3-(2-hydroxy-acetyl)-3a,6-dimethyl-7-oxo-dodecahydro-cyclo-penta[alpha]naphthalen-6-yl]-propionic acid having a molecular weight of 382 Daltons ($C_{20}H_{30}O_7$), designated as Deina®. The purpose of this new use is the regeneration of atrophic tissues, in vitro and in vivo, in human and veterinary contexts, in particular of atrophic cutaneous, mucosal and connective tissues, preferably in the course of atrophy complicated by inflammatory and/or calcified states and even more preferably in the eutrophic restoration of tissues of ectodermic derivation.

According to this invention this object is accomplished through the solution specifically claimed in the following claims. The claims form an integral part of the technical teaching provided here in connection with the invention.

The inventors have found that the molecules according to the invention are effective in inducing the repair and regeneration of atrophic conditions such as atrophic cutaneous tissue, mucosal tissue and connective tissues, both in vitro and in vivo, through the restoration of optimum physiological, biochemical and microenvironmental conditions to stimulate vitality and improve trophism in the compromised tissues, including in the course of atrophy complicated by pathological inflammation and/or calcification. More particularly the inventors have found that use of the compound having the chemical formula claimed above is effective in the reparative/regenerative infra-lesional and peri-lesional treatment of cutaneous, subcutaneous, mucosal, connective and preferably vascular and/or cartilaginous and/or peripheral nervous tissues and/or integumentary system and mucosal tissue in general, and also has a chelating action for calcium and calcified endovascular and tissue plaques.

The invention is based on observation of a particular anti-atrophic stimulus exerted by the compound Deina® derived from hydrocortisone on the skin and/or scalp and/or corresponding cutaneous appendages (hair) and/or the mucosa (all mucosa and/or gastro-intestinal lining mucosa and/or bronchial lining mucosa) and/or connective tissue and/or nervous tissue. This activity is induced through interaction with local-regional receptors for the substances capable of inducing recovery of the trophism of atrophic tissue [1, 2].

The activity of the compound Deina® described in the invention may be usefully applied in both the cosmetic and medical fields to restore atrophic conditions to microenvironmental and cellular eutrophic conditions with the recovery of normal physiological tissue functions.

In the cosmetic field, these substances may be used in mammals for the anti-atrophic treatment of wrinkles, for recovery of the original pigmentation of cutaneous appendages (hair), including in human beings, and to stimulate the growth of cutaneous appendages when dependent on the atrophic pathology; for anti-atrophic treatment of the skin and subcutaneous tissues whether simple or complicated by inflammatory conditions (creams, gels, foams, lotions or patches); for the anti-atrophic treatment of the gastro-intestinal mucosa, whether simple or complicated by inflammatory conditions; for the anti-atrophic treatment of diseases of the respiratory apparatus, whether simple or complicated by inflammatory conditions; for the anti-atrophic treatment of blood diseases, whether simple or complicated by inflammatory conditions; for the anti-atrophic treatment of allergic conditions in dermatology when complicated by inflammatory conditions; for the anti-atrophic treatment of cardiomyopathic diseases and peripheral vascular diseases, whether simple or complicated by inflammatory conditions and calcified pathological conditions; for the anti-atrophic treatment of painful musculoskeletal conditions, and muscular conditions, whether simple or complicated by inflammatory conditions and calcified pathological conditions (myalgias in general, headaches); for the anti-atrophic treatment of tissue dystrophy dependent upon adversely affected collagen synthesis, whether simple or complicated by inflammatory conditions and calcified pathological conditions (dermatological diseases, ophthalmic diseases in general, diseases of the ear, nose and throat, diseases of cartilage in general and joints in particular); for the anti-atrophic treatment of painful conditions in general when complicated by inflammatory conditions and calcified pathological conditions.

In the medical field the hydrocortisone derivative compounds may be used systemically (parenterally and/or percutaneously and/or as infusions and/or orally and/or rectally) in conditions having an atrophic component of an inflammatory-ischaemic-degenerative and/or calcifying type:

for the treatment of pain in general;
for the treatment of chondropathies and arthropathies, diseases of the tendons, connective tissues and rheumatic diseases in general, whether acute or chronic, degenerative or not, always complicated by micro-ischaemia and peri-lesional atrophy;
for the treatment of collagen diseases of an atrophic nature;
for the treatment of muscular conditions and musculoskeletal diseases in general, whether degenerative or not, dependent on micro-ischaemia;
for treatment of diseases of the soft tissues having an ischaemic-atrophic aetiopathogenic component;
for the treatment of dermatological diseases, of an atrophic-dystrophic nature;
for the treatment of allergy, with atrophic progression;
for the treatment of acute or chronic, atrophic, inflammatory or degenerative ophthalmic diseases;
for the regenerative treatment of atrophic cutaneous tissue and scalp in patients who have suffered damage to these tissues, or for the treatment of effluvium or defluvium alopecia;
for the treatment of atrophic neuro-degenerative conditions;
for the treatment of headaches and migraines of ischaemic-atrophic nature;
for psychostimulant, ionotropic and neuroleptic treatment in the course of diseases of the Central Nervous System of an ischaemic-atrophic nature;
for the treatment of painful neoplastic-ischaemic conditions, including when complicated by metastases;
for the treatment of adrenal atrophy conditions with cortico-adrenal insufficiency, with or without loss of endocrine stimulation;
for the treatment of shock conditions of an atrophic-ischaemic nature;
for the treatment of central and/or peripheral vascular diseases having a micro- and/or macro-ischaemic-atrophic aetiology;
for the treatment of haematological, cardiovascular and respiratory conditions of an auto-immune nature, with an atrophic progression;
for the treatment of gastrointestinal diseases with an atrophic progression;
for the treatment of oedematous conditions with an atrophic progression;
for the treatment of atrophies or dystrophies of the corpus cavernosum, whether simple or complicated by reactive calcification or fibrosis, with or without chronic inflammation;
for the treatment of thyroid diseases, with an atrophic-dystrophic progression.

Preferably, the invention describes a new use of the planar molecule:
IUPAC name: 3-[3,5-Dihydroxy-3-(2-hydroxy-acetyl)-3a, 6-dimethyl-7-oxo-dodecahydro-cyclo-penta[alpha] naphthalen-6-yl]-propionic acid having a molecular weight of 382 Daltons ($C_{20}H_{30}O_7$), designated as Deina®.

The molecule designated as Deina®, which belongs to the class of molecules having biological activity derived from propionic acid, belonging to the class of molecules having biological activity derived from propionic acid, has marked eutrophicating, anti-atrophic anti-inflammatory and anti-calcificatory abilities relating to cutaneous and mucosal connective tissues and rheological ability with regard to tissues of an ectodermic derivation in general.

Further ingredients suitable for use in the composition according to the invention are:
a solution of amine-ester and amine-amide anaesthetics, preferably 2% lidocaine;
physiological saline;
water for injectable preparations.

According to the intended applications and uses the compositions according to the invention may be provided as pharmaceutical compositions (in different tissue-specific formulations), medical devices, cosmetic compositions or as cell culture media for use in vitro.

As will be described in greater detail, the composition according to the invention has been tested both in vitro and in vivo. The results obtained confirm its effectiveness in the repair, regeneration and retrophication of atrophic tissues, including inflamed, ischaemic and/or necrotic tissues such as the skin, mucosa, subcutaneous tissues and connective tissue in general. The histological results obtained in vitro are particularly significant. Repair and retrophication of tissues brought about by the solutions according to the invention are morphologically comparable with the eutrophic condition of intact tissues in vivo, with optimum histo-functional characteristics. With normal in vitro culture media tissues from skin biopsies frequently do not survive for a month [3].

DETAILED DESCRIPTION OF THE INVENTION

This invention provides a valid and effective solution for the treatment of atrophic tissues, including inflamed, ischaemic and/or necrotic tissues, favouring the proper synthesis, metabolism and catabolism of collagen and accelerating tissue repair.

In particular this invention provides a valid and effective solution for improving the vitality and trophism of epidermal, dermal, mucosal and connective tissues in general when compromised by atrophy, post-ischaemic inflammation and/or necrosis, through the creation of conditions which favour cell repair, regeneration and differentiation.

The invention is based on the surprising observation of a particular proliferative stimulus exerted by the active ingredients described above.

These active ingredients have a double action which is anti-microbial, as a result of its acid pH, and one of regulating collagen metabolism and catabolism, encouraging eutrophism of cutaneous, mucosal and connective tissue and proper local-regional vascular and nervous regeneration, together with balanced cell proliferation, and finally a chelating action towards calcium salts encouraging the dissolution of endovascular, perivascular and general calcifying tissue lesions.

The compositions used for the applications according to this invention have been prepared using the planar molecule of molecular weight 382 Daltons (C20H30O7), whose IUPAC name is 3-[3,5-Dihydroxy-3-(2-hydroxy-acetyl)-3a,6-dimethyl-7-oxo-dodecahydro-cyclo-penta[alpha]naphthalen-6-yl]propionic acid, designated as Deina®, as the active ingredient and at least one from amino acids, peptides, vitamins, vitamin factors, salts, anaesthetics, mucopolysaccharides, sugars; their alcohol derivatives and their mixtures, solutions for cell culture and essential oils as ancillary substances.

Deina® is used in quantities between 0.01 mg/ml and 100 mg/ml, preferably between 0.1 mg/ml and 20 mg/ml, even more preferably between 0.5 mg/ml and 10 mg/ml for substantially solid compositions and substantially liquid compositions.

Diseases of the cutaneous and subcutaneous tissue of an atrophic or dystrophic nature can be treated through the application of Deina®. The dermatological diseases which can be treated with the above compositions are indicated purely by way of a non-limiting example: pemphigus, Stevens Johnson syndrome, exfoliative dermatitis, herpetiform bullous dermatitis, seborrhoeic dermatitis and dermatitis in general, fungoid mycosis, psoriasis, acne vulgaris, especially in the presence of inflammatory complications and lesions.

As regards the use of Deina® and ancillary substances in the treatment of alopecia, use which was partly claimed in patent PCT/IB2008/002562, it is specified by way of non-limiting example that there are forms of alopecia of an exclusively atrophic-degenerative nature not previously claimed such as: alopecia induced by drugs, chemotherapy, heavy metals, intoxication and autoimmune alopecia.

By way of the use of Deina® and ancillary substances in the treatment of atrophic degeneration of cutaneous and subcutaneous tissues in the form of complications of chronic allergic conditions mention will be made by way of non-limiting examples of: asthmatic conditions, bronchial asthma, contact dermatitis, atrophic dermatitis, allergic rhinitis, perennial rhinitis, hypersensitivity reactions to drugs and in particular iatrogenic urticaria-like reactions.

With regard to ophthalmic diseases of a degenerative-atrophic nature, mention will be made by way of non-limiting examples of: specific and non-specific and allergic inflammatory processes of the eye and its appendages, uveitis, retinitis, calcification of the sclera, conjunctivitis, keratoconjunctivitis, blepharitis, dacryocystitis, blepharoconjunctivitis, episcleritis, scleritis, post-operative reactions, inflammatory conditions including those associated with painful conditions and not of an infectious nature affecting the anterior segment of the eye, inflammation of the anterior uvea—iritis, iridocyclitis, scleritis, episcleritis and myositis, cataracts.

With regard to the treatment of diseases of mucosal tissue of a degenerative-atrophic nature through the use of Deina® mention may be made by way of non-limiting examples of gastrointestinal diseases, ulcerous colitis, Crohn's disease, irritable colon, acute and chronic intestinal idiopathic phlogosis of anorectal and perianal location, spastic-painful conditions of the digestive tract, regional enteritis, anal itching, colitis, functional colonic disease, ulcerous proctitis, and the symptoms and complications of haemorrhoids.

With regard to treatment of atrophic-degenerative diseases of the respiratory tract these include by way of non-limiting examples: sarcoidosis, Loeffler's syndrome, berylliosis, aspiration pneumonia, pulmonary emphysema complicated by bronchospasm, pulmonary oedemas, Hamman-Rich syndrome.

With regard to the use of Deina® and ancillary substances in the treatment of atrophic degeneration of mucosal tissue in the form of complications of chronic allergic conditions mention may be made by way of non-limiting examples of: asthmatic conditions, bronchial asthma, allergic rhinitis, perennial rhinitis, and drug hypersensitivity reactions.

Diseases of the connective tissue of an atrophic-degenerative nature can be treated by direct administration. By way of non-limiting examples reference may be made to diseases, including those having a rheumatic aetiopathogenesis, such as chondropathy and arthropathy of the tendons and connective tissues including: synovitis due to osteoarthritis, correlated rheumatoid arthritis degeneration, acute and subacute bursitis, epicondylitis, fibromyositis, tenosynovitis, non-specific acute tenosynovitis, Dupuytren's disease, post-traumatic osteoarthritis, periarticular calcification, acute gouty arthritis, psoriatic arthritis, ankylosing spondylitis, clicky finger, tendon cysts, Beker cysts, carpal tunnel, tendonitis, peritendonitis, De Quervain's disease and lipomas.

With regard to atrophic degenerative diseases of collagen treated with Deina® these include by way of non-limiting examples systemic lupus erythematosis and sclerodermia.

Among the diseases of the soft tissues of an atrophic-degenerative nature which can be treated by injection treatment mention may be made by way of non-limiting example of: intercostal neuritis, calcification of the soft tissues, neuralgia, ischialgia, radiculitis, diabetic polyneuritis, alcoholic polyneuritis, obliterating arterial disease of the limbs due to ischaemia and/or gangrene, cervical spondylitis, distortion, myalgia, strained muscles, back pain, sciatalgia, fibrositis, dysmenorrhoea.

The headaches and migraines of an ischaemic-atrophic nature treated with the new use which is the subject of this invention for Deina®, comprise by way of non-limiting examples accessional congestive headaches, typical migraines, vaso-motor headache migraines.

With regard to the treatment of atrophic neurodegenerative conditions mention may be made as non-limiting examples of amyotrophic lateral sclerosis, multiple sclerosis (support treatment), Parkinson's disease and syndrome (support treatment), myasthenia gravis, comatose conditions and coma, demyelinising chronic inflammatory polyradiculoneuropathy, multifocal motor neuropathy.

With regard to atrophic-degenerative blood and cardiovascular diseases the following are included in treatment with Deina® and ancillary substances by way of non-restrictive examples: autoimmune haemolytic anaemia, purpura, secondary thrombocytopenia, erythroblastopenia, erythroid anaemia, Biiger's disease, Raynaud's disease and phenomenon, rheumatic carditis.

With regard to atrophic-degenerative diseases of the corpus cavemosum complicated by inflammatory and/or calcifying conditions the following are included in treatment with Deina® and ancillary substances by way of non-limiting examples: calcification of the corpus cavemosum, fibrosis of the corpus cavernosum, priapism.

With regard to painful neoplastic-ischaemic conditions complicated by atrophic degeneration the following can be treated by injection treatment by way of non-limiting examples: bony metastases, prostate adenocarcinoma, primary or secondary located or diffuse neoplasms in general.

With regard to pain relief treatment in general, where the pain accompanies atrophic degeneration of compromised tissue, mention may be made by way of non-limiting examples of: spasms of striated muscle, in particular those deriving from protracted febrile states during childhood, muscular atrophy due to post-comatose or post-traumatic conditions or degenerative diseases of the central nervous system or extrapyramidal syndromes or spastic contraction of the skeletal musculature or myodystrophy or correlated vertebral postures for reducing arthritic pain and in particular of the neck or intevertebral compressible disc diseases or skeletal trauma with tissue degeneration or primary or secondary neoplasms.

Of the atrophic degenerations following oedematous conditions which can be treated with Deina®, mention may be made by way of non-limiting examples of: cerebral oedema having various aetiologies, primary tumour oedema, metastasis and recurrent oedema, oedema due to vascular accidents, post-surgical oedema, traumatic oedema and pseudotumour oedema.

The compositions to which this invention relates have been prepared using the active ingredients specified below.

Active Ingredients

1. Hydrocortisone Derivatives

The planar molecule of molecular weight 382 Dalton, whose IUPAC name is 3-[3,5-Dihydroxy-3-(2-hydroxy-acetyl)-3a,6-dimethyl-7-oxo-dodecahydro-cyclo-penta[alpha]naphthalen-6-yl]-propionic acid, designated as Deina®.

Ancillary Substances (Non-Obligatory)

1. Amino Acids

Methionine, cystine, N-acetylcysteine, cystine, glycine, leucine, isoleucine, proline, glutamine, arginine, glutamic acid, histidine, histidine-HCl—$H_2O$, lysine, lysine-HCl, phenylalanine, serine, threonine, tryptophan, tyrosine, tyrosine-disodium salt, valine, proline, hydroxyproline, solution containing all non-essential amino acids.

2. Peptides

Glutathione, collagen, elastin, yeast extract, polypeptides to which trophic functions are attributed.

3. Vitamins

Retinoic acid, retinol, ascorbic acid, pantothenic acid, D-calcium pantothenate, pyridoxine, pyridoxine-HCl, folic acid, nyacinamide, riboflavin, cobalamine, para-aminobenzoic acid and biotin.

4. Vitamin Factors

Inositol, myo-inositol, choline chloride, pyruvic acid, sodium pyruvate.

5. Salts

Calcium gluconate, calcium phosphate, sodium dicarbonate, calcium chloride, magnesium chloride, magnesium sulphate, potassium chloride, potassium phosphate, sodium chloride, calcium nitrate, zinc chloride, ferric nitrate, sodium pyruvate, D-calcium pantothenate, tyrosine disodium salt.

6. Anaesthetics

Amine-ester and amine-amide anaesthetics used as listed below.

I. Amine-Amide Anaesthetics

Articaine: methyl-4-methyl-3-(2-propylaminopropanoylamino)thiophen-2-carboxylate;
Bupivacaine: 1-butyl-N-(2,6-dimethylphenyl)piperidin-2-carboxyamide;
Carticaine: methyl-4-methyl-3-(2-propylaminopropanoylamino)thiophen-2-carboxylate;
Cinchocaine: 2-butoxy-N-[2-(diethylamino)ethyl]quinoline-4-carboxyamide;
Hexylcaine: 1-(cyclohexylamino)propan-2-yl benzoate;
Etidocaine: N-(2,6-dimethylphenyl)-2-(ethyl(propyl)amino)butanamide;
Levobupivacaine: (S)-1-butyl-N-(2,6-dimethylphenyl)piperidin-2-carboxyamide;
Lidocaine (Lignocaine, Xylocaine): 2 (diethyl amino)-N-(2,6-dimethylphenyl)acetamide;
Mepivacaine (carbocaine or polocaine): N-(2,6-dimethylphenyl)-1-methyl-piperidin-2-carboxyamide;
Piperocaine (methicaine): 3-(2-methyl-1-piperidyl)propyl benzoate;
Prilocaine: N-(2-methylphenyl)-N2propyl-alaninamide;
Ropivacaine: (S)—N-(2,6-dimethylphenyl)-1-propylpiperidin-2-carboxyamide;
Trimecaine: $N^2,N^2$-diethyl-N-mesitylglycinamide.

II. Amine-Ester Anaesthetics

Amylocaine: 1-(dimethylaminomethyl)-1-methylpropyl benzoate;
Benzocaine: ethyl-4-aminobenzoate;
Chloroprocaine (nesacaine): 2-diethylaminoethyl-4-amino-2-cloro-benzoate.
Cocaine: methyl-(2R,3S)-3-benzoyloxy-8-methyl-8-azabicyclo[3.2.1]octan-2-carboxylate;
Cyclomethycaine (topocaine): 3-(2-methyl-1-piperidyl) propyl 4-cyclohexyloxybenzoate;
Dimethocaine (Larocaine): (3-diethylamino-2,2-dimethylpropyl)-4-aminobenzoate;
Meprylcaine (epirocaine or oracaine): (2-methyl-2-propylamino-propyl)benzoate;
Orthocaine: methyl 3-amino-4-hydroxy-benzoate;
Procaine (Novocaine): 2-(diethylamino)ethyl-4-aminobenzoate;
Propoxycaine: 2-diethylaminoethyl-4-amino-2-propoxybenzoate;
Proxymetacaine (Proparacaine): 2-diethylaminoethyl-3-amino-4-propoxy-benzoate;
Risocaine: propyl-4-aminobenzoate;
Tetracaine (amethocaine or Pontocaine):2-(dimethylamino)ethyl-4-(butylamino)benzoate.

7. Mucopolysaccharides

Hyaluronic acid, chondroitin sulphates.

8. Sugars, Their Alcohol Dderivatives and Their Mixtures

Glucose, saccharose, glucanes, mannanes, glucomannanes, fucose, fructose, heparan sulphates, pectin, starches, their alcohols and derivatives.

9. Solutions for Cell Culture

RPMI 1640 (this is a base medium for the culture of mammalian cells), DMEM-LG (DMEM is a modification of the Eagle essential minimum medium (EMEM) containing amino acids, salts, glucose, vitamins and iron; LG indicates that the glucose concentration is low), FBS (foetal bovine serum), F12 (solution for cell cultures containing a complete source of amino acids), Hank's solution (solution for cell cultures containing sodium bicarbonate).

10. Essential Oils

Essential oils suitable for use in a composition according to the invention are for example hypericum, borage, mint, ginger, lavender, calendula, horse chestnut, grapefruit, cedar, pine, myrrh, incense and amber oils.

COMPOSITIONS

The compositions to which this invention relates (hereinafter referred to as Deina®) for in vitro and in vivo use have been prepared using the substances in the quantities indicated purely by way of example in Tables 1 to 5.

TABLE 1

Deina ® composition for in vitro use

| Substance | Concentration mg/L |
|---|---|
| Active ingredients | |
| Deina ® | 10 mg |
| Further active ingredients | |
| Glucose | 1 g |
| RPMI 1640 or DMEM-LG | q.s. for one litre of solution |
| PCS | 50 ml |
| F12 | 10 ml |
| Hank's solution | 20 ml |
| MEM solution—non-essential amino acids | 20 ml |

TABLE 2

Deina ® for in vivo endovenous use

| Substance | Concentration |
|---|---|
| Active ingredients | |
| Deina ® | 10 mg |
| Further active ingredients | |
| Physiological saline | 20 ml |

TABLE 3

Deina ® for in vivo parenteral use

| Substance | Concentration |
|---|---|
| Active ingredients | |
| Deina ® | 10 mg |
| Further active ingredients | |
| Physiological saline | 4 ml |
| Lidocaine 2 mg/L | 1 ml |

TABLE 4

Deina ® gel for in vivo topical use

| Substance | Concentration |
|---|---|
| Active ingredients | |
| Deina ® | 20 mg |
| Further active ingredients | |
| BASE in gel (carbopol or cellulose derivatives) | q.s. per kg of product |

TABLE 5

Deina ® cream for in vivo topical use

| Substance | Concentration |
|---|---|
| Active ingredients | |
| Deina ® | 20 mg |
| Further active ingredients | |
| BASE in the form of cream or emulsion (O/W or W/O) (such as: water, white vaseline, cetostearyl alcohol, liquid paraffin, ceteth-20, sodium phosphate, p-chloro-m-cresol, phosphoric acid) | q.s. per kg of product |

Rationale for the Composition

This invention is based on the observation of a particular reparative and regenerative stimulus acting on the skin, mucosa, subcutaneous tissues and connective tissues by the molecule designated as Deina® alone or in combination with one or more further active ingredients selected from: amino acids, peptides, vitamins, vitamin factors, salts, anaesthetics (amine-ester or amine-amide), mucopolysaccharides, sugars, or solutions for cell cultures. Further ingredients selected on the basis of the nature of the dosage and the specific medical indication in question, such as for example mucopolysaccharides, antibiotics, amine-amide anaesthetics or essential oils, may also be present in the compositions according to the invention.

Cosmetic and pharmaceutical compositions and compositions of the medical device type to which this invention relates may also comprise further accessory elements such as excipients and vehicles, the choice and use of which will fall within the scope of an average person skilled in the art without this requiring any inventive step.

The compositions according to the invention prepared as culture media have been tested to check their effectiveness in preserving the vitality of atrophic bioptic samples.

In vitro histological results obtained in both the short term (7 days) and up to two months of culture with the composition described in Table 1 have confirmed the formation of morphologically optimum eutrophic tissue persisting over time in all the biopsies treated.

All atrophic cicatricial bioptic tissue samples tested responded positively to the use of culture media according to the invention, remaining vital, reorganising the three-dimensional tissue structure and depositing collagen in a physiological way with an ordered three-dimensional redistribution during at least six months culture in vitro.

A clinical trial to evaluate tolerance and efficacy for the compound known as infusional Deina® (composition shown in Table 3) was also performed on a compassionate basis.

Finally, a clinical trial to evaluate tolerance and efficacy for the compound known as Deina® cream (composition shown in Table 5) was performed on a compassionate basis.

Without wishing to be bound by any specific theory in this respect, these inventors take the view that the results obtained with the culture media according to this invention have demonstrated that the condition of atrophy in the course of degenerative processes can be reversed.

According to this invention the culture media may include further ingredients such as for example the usual inorganic salts, sugars, peptides, amino acids and vitamins required for the maintenance and/or growth of mammalian cells in culture, as well as any antibiotic and/or antimicroorganism agents necessary to prevent contamination of the cultures.

The examples which follow are provided purely by way of illustration and without restriction of the scope of this invention as defined in the appended claims.

CONCLUSIONS

Use of the compound Deina® has demonstrated that atrophic diseases whether simple or complicated by chronic inflammation or reactive calcification can be resolved both in vitro and in vivo.

Use of the compound Deina® has also demonstrated optimum tolerance in all patients treated, without any apparent effect of a systemic nature, regardless of differences in age, build, sex and location of the treatment.

EXAMPLE 1

Biopsies and Prototype Solutions
Biopsies
The bioptic animal samples in the investigation comprised biopsies of:
  chronic atrophic cutaneous lesions due to venous stasis (base and margins),
  damaged joint cartilage (chronic degenerative osteo-articular arthritis),
  terminal cicatricial scalp (post-traumatic or surgical lesions),
  hyperkeratosis of the oral cavity (vitamin B deficiency).

All the samples were washed three times with physiological saline and antibiotics (100 units/ml of penicillin+100 μg/ml of streptomycin+160 mg/L gentamycin, fluconazole 0.2 mg/ml) for 10 minutes at ambient temperature.

The biopsies were then sectioned into three parts (two controls, 1 and 2, and one sample, 3, to be treated for each patient) and suspended in a final volume of 25 ml of the corresponding culture solutions within 10 cm slides (Lab-Tek chamber slides, Nunc, Kamstrup, Denmark).

Two types of controls were prepared, an untreated negative control (1), that is one treated with physiological saline and antibiotics only (as described above), and a positive control (2) treated with media for ordinary cell culture for skin biopsies.

1. Negative control: Bioptic controlled specimens 1 were suspended in physiological solution between 10 cm slides (Lab-Tek chamber slides, Nunc, Kamstrup, Denmark).

2. Positive control: Controlled bioptic specimens 2 were placed between 10 cm slides (Lab-Tek chamber slides, Nunc, Kamstrup, Denmark) in D-MEM medium supplemented with:
  10% FBS (Celbio, Milan, Italy)
  160 mg/L gentamycin (Schering-Plough, Milan, Italy)
  2 mM L-glutamine (Life Technologies; growth medium)
  50 ng/mL EGF (Epidermal Growth Factor, Sigma Aldrich, Milan, Italy) for skin, mucosal and scalp biopsies,
  20 ng/mL TGF-beta 1+20 μg TGF-beta 3 (Transforming Growth Factor beta, Sigma Aldrich, Milan, Italy) for cartilaginous biopsies.

3. Samples-1 and -2. Bioptic samples 1 and 2 were placed between 10 cm slides (Lab-Tek chamber slides, Nunc, Kamstrup, Denmark) in medium in a solution of Deina® culture medium (double test).

All the samples were incubated for 15 days in a Heraeus incubator thermostatically controlled to a temperature of 37° C. with an atmosphere containing 5% of constantly provided $CO_2$ (v/v in air). 2/3 of the culture medium was replaced every 7 days. All the bioptic tissues used in the culture constitute a possible optional co-conditioning support for three-dimensional growth of the cell samples studied.

Staining Protocol

After three washes for 10 min at ambient temperature in PBS (pH 7.4), the samples were resuspended in 4% paraformaldehyde fixing solution in D-MEM (Gibco) at a pH of 7.4, for 1 hour at ambient temperature. All the biopsies involved in the study were treated with Alcian Blue. This stain comprises a group of multipurpose basic water-soluble stains. The colour blue is due to the presence of copper in the molecule. Alcian Blue in solution in PBS (pH 7.4) in a final concentration of 1% w/V was added to a 3% solution of acetic acid (pH 2.5). After incubation for 2 hours at ambient temperature this composition became indelibly stained binding the acid mucopolysaccharides and both the sulphonate and carboxylate glycoproteins. Specific controls were prepared for each sample. All the samples were washed 3 times with PBS (pH 7.4) at ambient temperature for five minutes and then observed under an optical microscope. A net increase in type 2 and type 4 collagen, which became coloured blue, was noted in samples 1 and samples 2 treated with Deina® culture medium in comparison with control 1 and control 2 [2].

Results

Staining with the Alcian Blue Colourimetric Method

Negative controls 1 treated with physiological saline: diffuse blue colouration (score=++++) alternating with cytolytic and necrotic areas.

Positive controls 2 treated with ordinary biopsy culture medium as described above. Very strong diffuse blue colouration noted (Alcian Blue, (score=+++++)).

Samples treated with Deina® culture medium solution. It was noted that the cells in which redeposition of mucopolysaccharides in glycoprotein was brought about were clearly stained with Alcian Blue growing in overlapping layers and ordered with a physiological distribution of mucopolysaccharides and GAG (score=+++++).

Optical Microscopy

These results indicate tissue reactivation or regeneration in the bioptic samples for treatment groups (Sample 1 and Sample 2 (Deina®)). Results relating to the expression of cytokeratin 10 and 11 and histological staining of the bioptic preparations with haematoxylin/eosin (used to display skin, chondrocyte, mucosal and follicular vitality) are shown in Table 6 (CONTROLS) and Table 7 (SAMPLES), and have been expressed using a qualitative and semi-quantitative scale.

From an examination of the results in Table 7 it will be seen that under optical microscopy (staining with eosin and haematoxylin) there was a net increase in the number of cells in the samples treated for two months belonging to the treatment group (Deina®). In addition to this all the tissues appeared to be trophic, vital and active in the samples included in the Sample treatment group (Deina®) in comparison with controls. Finally there is a net predominance of cytokeratin 10 and 11, typical of normal tegument tissues and scalp tissues having vital follicles (Table 7).

Table 6.

Controls belonging to type 1 and controls belonging to type 2: the median day of irreversible necrosis is day 15 for the controls belonging to type 1. The median day for irreversible necrosis is equal to day 60 for the controls belonging to type 2.

TABLE 6

| Markers | Control 1 day 7 | Control 1 day 15 | Control 2 day 7 | Control 2 day 60 |
|---|---|---|---|---|
| Cytokeratin 10 | — | + | +++ | ++ |
| Cytokeratin 11 | −/+ | + | +++ | + |
| Nuclei/cytoplasma conserved Eosin/Haematoxylin | massive necrosis | diffuse necrosis | trophic tissues | vacuolar necrosis |

Key
— = no fluorescence
+ = slight fluorescence in the optical field
++ = some fluorescence in the optical field
+++ = medium fluorescence in the optical fluorescence field in the optical field
++++ = high fluorescence in the optical field
+++++ = diffuse fluorescence in the optical field Table 7.

Samples belonging to the type of the Sample treatment group (Deina®). Median semi-quantitative values for incubation days 7 and 60.

TABLE 7

| Markers | Samples 1 day 7 | Samples 1 day 60 | Samples 2 day 7 | Samples 2 day 60 |
|---|---|---|---|---|
| Cytokeratin 10 | +++ | +++++ | +++ | +++++ |
| Cytokeratin 11 | +++ | +++++ | +++ | +++++ |
| Nuclei/ cytoplasma conserved Eosin/ Haematoxylin | optimum morphology | optimum morphology | optimum morphology | optimum morphology |

Key
— = no fluorescence
+ = slight fluorescence in the optical field
++ = some fluorescence in the optical field
+++ = medium fluorescence in the optical fluorescence field in the optical field
++++ = high fluorescence in the optical field
+++++ = diffuse fluorescence in the optical field Western Blot The samples were subjected to phenotype analysis by Western Blot for the markers (Santa Cruz Biotechnology, America, California) and type I collagen, type II anti-collagen, type IV anti-collagen, anti-cytokeratins 1, 5, 8, 10, 14, 15, 18, 19 and anti-aggrecan. After five washes the membranes were incubated with the corresponding secondary antibodies (1:1000) conjugated with horseradish peroxidases (HRP, Santa Cruz, Calif., USA) for 1 hour at ambient temperature, as shown in Table 10 below.

Characterisation of Biopsies of Atrophic Skin Treated with Deina® Culture Medium Versus Controls Other expressions of type I collagen indicate a tendency to hypertrophic regeneration. High CK10 and CK14 expressions indicate a strong keratosic component and atrophy of the cutaneous tissue. The results relating to type I collagen, type IV collagen and cytokeratin 1, 5, 10 and 14 expression are shown on a quantitative scale as follows:

TABLE 8

| Markers | Control 1 | Control 2 | Sample 1 | Sample 2 |
|---|---|---|---|---|
| Type I collagen | −/+ | +++ | +++ | +++ |
| Type IV collagen | −/+ | +++ | +++ | +++ |
| Cytokeratin 1 | ++++ | +++ | +++++ | +++++ |
| Cytokeratin 5 | ++++ | +++++ | +++++ | +++++ |
| Cytokeratin 10 | ++++ | +++++ | +++ | +++ |
| Cytokeratin 14 | +++++ | ++ | ++ | ++ |

Key
— = no band
−/+ = slight presence of a band
+ = thin band present
++ = medium band present
+++ = extensive band present
++++ = tall band present
+++++ = effusive band present Characterisation of Atrophic Cartilaginous Biopsies Treated with Deina® Culture Medium Versus Controls Low expression of type II collagen and aggrecan indicate cartilaginous degeneration without atrophy, dystrophy and loss of mass. The results relating to type II and aggrecan expression have been expressed on a quantitative scale as follows:

TABLE 9

| Markers | Control 1 | Control 2 | Sample 1 | Sample 2 |
|---|---|---|---|---|
| Type II collagen | −/+ | +++ | +++++ | +++++ |
| Aggrecan | ++ | +++ | +++++ | +++++ |

Key
— = no band
−/+ = slight presence of a band
+ = thin band present
++ = medium band present
+++ = extensive band present
++++ = tall band present
+++++ = effusive band present Characterisation of Atrophic Mucosa and Hyperkeratosis Biopsies Treated with Deina® Culture Medium Against Controls A high expression of cytokeratin (or CK) 10 and CK14 and type I collagen indicates high mucosal keratinisation. The results relating to type I collagen, type IV collagen and CK1, CK5, CK10 and CK14 expression have been expressed on a quantitative scale as follows:

TABLE 10

| Markers | Control 1 | Control 2 | Sample 1 | Sample 2 |
|---|---|---|---|---|
| Type I collagen | + | ++++ | ++ | ++ |
| Cytokeratin 1 | +++ | +++++ | +++ | +++ |
| Cytokeratin 5 | ++++ | +++++ | ++++ | ++++ |
| Cytokeratin 10 | +++ | +++++ | ++++ | ++++ |
| Cytokeratin 14 | ++++++ | ++++ | ++ | ++ |

Key
— = no band
−/+ = slight presence of a band
+ = thin band present
++ = medium band present
+++ = extensive band present
++++ = tall band present
+++++ = effusive band present Characterisation of Scalp with Bulbar Atrophy and Post-Scarring Tissue Biopsy Treated with Deina® Culture Medium Against Controls High expressions of cytokeratin (or CK) 15 and type IV collagen indicate high atrophy of the hair forming bulb. It is known that staminal cells of the skin are positive to cytokeratin 19 (CK19). The expression CK19 may be used as an indicator of the staminal cells present in hair-forming follicles and cell cultures of these hair-forming follicles. Results relating to the expression of type I collagen, type IV collagen and CK1, CK5, CK10 and CK14 are expressed on a quantitative scale as follows:

TABLE 11

| Markers | Control 1 | Control 2 | Sample 1 | Sample 2 |
|---|---|---|---|---|
| Type I collagen | + | ++++ | ++ | ++ |
| Type IV collagen | ++++ | +++ | ++ | ++ |
| Cytokeratin 1 | +++ | +++++ | +++ | +++ |
| Cytokeratin 5 | ++++ | +++++ | ++++ | ++++ |
| Cytokeratin 10 | + | +++ | +++ | +++ |
| Cytokeratin 11 | +++ | ++++ | ++ | ++ |
| Cytokeratin 15 | ++++++ | ++++ | ++ | ++ |
| Cytokeratin 19 | ++++ | ++++ | ++++ | ++++ |

Key
— = no band
−/+ = slight presence of a band
+ = thin band present
++ = medium band present
+++ = extensive band present
++++ = tall band present
+++++ = effusive band present Histological results in vitro obtained in both the short term (7 days) and over a period of up to two months culture with the prototype solutions in Table 1 (Samples 1 and 2, Deina®) versus control 1 solutions (negative control, physiological) and control 2 (positive control, growth factors) confirm:

for all the biopsies treated with Deina® solution, referred to as Sample 1 and Sample 2, morphologically optimal eutrophic tissue formed and persisted over time, for all the biopsies treated with Control 1 solution, necrotic tissue formed, for all the biopsies treated with Control 2 solution, trophic tissue formed.

EXAMPLE 2

Deina® CREAM Formulations.
In Vivo Clinical Trial 1.

A clinical trial was performed to evaluate the tolerance and therapeutic efficacy of the products known as Deina® CREAM (compositions shown in Table 5) in the regeneration and repair of the skin and subcutaneous tissues.

This trial was performed on mammals in a sample comprising 20 dogs and 20 cats (of different breeds and size; 20 individuals for each breed treated with Deina® CREAM), and of different age and different breeds presenting with cutaneous lesions ascribable to tissue atrophy (dogs: consequences of lacerating and bruising wounds, consequences of surgical wounds, consequences of licking wounds and consequences of burns).

The individuals affected by the abovementioned lesions were selected at the inclusion examination.

The animals were brought to a clinical check examination weekly until they were cured and underwent a cytological examination and an evaluation of the extent and depth of the skin lesion.

The composition Deina® CREAM has been used in two daily applications for a period of not less than 35 days up to a maximum of 90 days. In no case was any allergy or intolerance phenomena encountered, indeed in most cases patients showed strong attenuation of the pruritis and pain a few days after initiating treatment. Hyperaemia was initially found in almost all patients as an effect of the surface vasodilation induced by the two compositions under investigation. This positive epiphenomenon may indicate partial resolution of the ischaemic condition found in the peri-lesional area. However, the hyperaemia progressively attenuated as treatment continued. In most patients total or almost total regression of the lesions was obtained (72%).

Good results were achieved with most atrophic lesions due to stasis (90%), with normalisation of colour and a reduction in dimensions.

In chronic post-traumatic lesions a significant reduction was found in these together with a recovery of substance (70%) together with macroscopic changes such as change in colour, attenuation of fibrous areas and spontaneous re-epithelisation.

Deina® Infusional Formulation.
In Vivo Clinical Trial 2.
Protocol
1. Enrolment
Twenty cases (dogs of different breed, size, body weight, sex and age).
2. Inclusion Criteria
Bilateral joint changes.
3. Clinical Procedure
The following procedures were adopted for all the dogs examined.
4. Procedure
The quantity of solution inoculated was equal to the quantity of synovial fluid aspirated and analysed.
a. Time Zero
Collection of case history and clinical examination comprising full blood counts, including LACTATES to check metabolic oxidation,
Radiography of the limb in question,
ROM (Range Of Motion),
Exploratory arthroscopy,
Exclusion of any intra-articular curettage,
Arthrocentesis with removal and morphological/cytological and biochemical examination of the synovial fluid,
Histological examination of a sample of joint cartilage,
Intra-articular inoculation of the solutions tested equal to the quantity of synovial fluid withdrawn and always in the same way (bilateral lesions): of Deina®.
A synovial examination and intra-articular injection of the solution was repeated weekly or for four/eight times, depending on the severity of the initial pathological condition.
b. End of the Treatment Cycle
Arthrocentesis with removal and morphological/cytological and biochemical examination of the synovial fluid,
Histological examination of a sample of joint cartilage,
Radiography of the joint in question,
ROM (Range Of Motion),
Blood lactic acid content,
Clinical examination and recording.

CONCLUSIONS

Use of the product designated as "Deina®" in the clinical trials carried out on 20 dogs of various breeds and size showed optimum tolerance in all patients without any apparent effect of the systemic type, regardless of differences in age, size, sex and joint location. ROM (Range of Motion) increased in 90% of cases, while clinical improvement occurred in 70%. Pain and palpation fell in 100% of cases. It should be emphasised that the relative ease of intra-articular inoculation is a matter of satisfaction to the owners of the 20 dogs treated.

Joint cartilage disease may affect patients of any age, but it becomes particularly important when it occurs in young patients engaging in an active life.

It is known that unlike bone tissue which has great regenerative capacity, hyaline cartilage, which is one of the main tissues in the musculoskeletal apparatus, is characterised by an absence of support from the blood, lymphatic and nervous systems, which is essential for tissue repair. In fact only small losses of substance are filled by fibrous-cartilaginous tissue, while those of larger size are infrequently filled.

Restoration of a physiological microenvironment results in reconstitution of normally functioning cartilaginous matrix in a short time.

REFERENCES

1. Costa A M, Peyrol S, Porto L C, Comparin J P, Foyatier J L, Desmouliere A. Mechanical forces induce scar remodeling. Study in non-pressure-treated versus pressure-treated hypertrophic scars. Am J Pathol. 1999 November; 155(5): 1671-9.
2. French M M, Smith S E, Akanbi K, Sanford T, Hecht J, Farach-Carson M C, Carson D D. Expression of the heparan sulfate proteoglycan, perlecan, during mouse embryogenesis and perlecan chondrogenic activity in vitro. J Cell Biol. 1999 May 31; 145(5):1103-15.
3. Robinson M, Reynolds A J, Gharzi A, Jahoda C A. In vivo induction of hair growth by dermal cells isolated from hair follicles after extended organ culture. J Invest Dermatol. 2001 September; 117(3):596-604.
4. Kafi R, Kwak H S, Schumacher W E, Cho S, Hanft V N, Hamilton T A, King A L, Neal J D, Varani J, Fisher G J, Voorhees J J, Kang S. Improvement of naturally aged skin with vitamin A (retinol). Arch Dermatol. 2007 May; 143 (5):606-12.
5. Rabinovitch M and De Stefano M J. Cell shape changes induced by cationic anesthetics. *J Exp Med.* 1976; 143: 290-304.

The invention claimed is:

1. A method of therapeutically treating an atrophic tissue in a subject, the atrophic tissue being selected from the group consisting of cartilage tissue and osteo-articular connective tissue, the method comprising administering to a subject in need thereof an effective amount of the compound 3-[3,5-Dihydroxy-3-(2-hydroxy-acetyl)-3α,6-dimethyl-7-oxo-dodecahydro-cyclo-penta[α]naphthalen-6-yl]-propionic acid or a pharmaceutically acceptable salt thereof.

2. The method according to claim 1, wherein the atrophy is of an inflammatory, ischaemic or degenerative nature.

3. The method according to claim 1, wherein the said compound is formulated in a pharmaceutical composition or medicament suitable for systemic, parenteral, percutaneous, infusional, oral or rectal administration.

4. The method according to claim 1, wherein the therapeutic treatment is selected from the group consisting of: pain relief treatment; the treatment of chondropathy and/or arthropathy; the treatment of chronic degenerative osteo-articular arthritis; the treatment of bilateral joint changes; the treatment of diseases of the central nervous system of an ischemic-atrophic type; the treatment of shock conditions of an atrophic-ischemic nature; the treatment of central and/or peripheral vascular diseases having a micro and/or macro-ischemic-atrophic aetiology or calcifications; the treatment of atrophy or dystrophy of the corpus cavernosum, whether simple or complicated by calcification or reactive fibrosis, with or without chronic inflammation; the treatment of atrophic tissue with calcifications; the treatment of diseases of the tendons; and the treatment of post-traumatic or surgical lesions.

5. The method according to claim 1, wherein the osteo-articular connective tissue is treated through stimulation of the regeneration and/or recovery of the original trophism, in the said connective tissue when the latter is in an original or reactive condition of simple or complicated atrophy of an inflammatory and/or ischaemic and/or degenerative and/or calcifying nature in a mammal.

6. The method according to claim 1, wherein the compound 3-[3,5-Dihydroxy-3-(2-hydroxy-acetyl)-3α,6-dimethyl-7-oxo-dodecahydro-cyclo-penta[α]naphthalen-6-yl]-propionic acid or pharmaceutically acceptable salt thereof is formulated in a pharmaceutical composition.

7. The method according to claim 6, wherein the compound 3-[3,5-Dihydroxy-3-(2-hydroxy-acetyl)-3α,6-dimethyl-7-oxo-dodecahydro-cyclo-penta[α]naphthalen-6-yl]-propionic acid or pharmaceutically acceptable salt thereof is at a concentration within the range from 0.01 mg/ml to 100 mg/ml.

8. The method according to claim 7, wherein the pharmaceutical composition is in a lyophilised, cream, gel, foam, serum, lotion, powder, patch, film or dressing form, in the form of an injection, in the form of an infused liquid, in the form of a suspension or emulsion, in the form of a spray, in the form of a tablet or suppository, or in any form suitable for oral, rectal, infusional, intramuscular, endovenous, transcutaneous, intra-ocular and endonasal administration.

9. The method according to claim 6, wherein the compound 3-[3,5-Dihydroxy-3-(2-hydroxy-acetyl)-3α,6-dimethyl-7-oxo-dodecahydro-cyclo-penta[α]naphthalen-6-yl]-propionic acid or pharmaceutically acceptable salt thereof is at a concentration within the range from 0.1 mg/ml to 20 mg/ml.

10. The method according to claim 6, wherein the compound 3-[3,5-Dihydroxy-3-(2-hydroxy-acetyl)-3α,6-dimethyl-7-oxo-dodecahydro-cyclo-penta[α]naphthalen-6-yl]-propionic acid or pharmaceutically acceptable salt thereof is at a concentration within the range from 0.5 mg/ml to 10 mg/ml.

* * * * *